United States Patent [19]
Ghent et al.

[11] Patent Number: 5,955,101
[45] Date of Patent: Sep. 21, 1999

[54] DRY STARCH-IODINE PHARMACEUTICAL FORMULATIONS

[75] Inventors: William R. Ghent, deceased, late of Inverary, Canada, by R. Alison Ghent, executor; Bernard A. Eskin, Bala Cynwyd, Pa.

[73] Assignee: 943038 Ontario Inc., Ontario, Canada

[21] Appl. No.: 08/743,202

[22] Filed: Nov. 5, 1996

Related U.S. Application Data

[63] Continuation-in-part of application No. 08/593,467, Jan. 29, 1996, which is a continuation-in-part of application No. 08/272,308, Jul. 8, 1994, abandoned, which is a continuation of application No. 07/961,038, Oct. 14, 1992, abandoned, which is a continuation of application No. 07/676,170, Mar. 28, 1991, abandoned.

[51] Int. Cl.$^6$ ................................................ A61K 33/18
[52] U.S. Cl. .................... 424/451; 424/464; 424/465; 424/667; 424/668; 424/499; 424/669
[58] Field of Search ....................... 424/451, 464, 424/465, 499, 667, 668, 669; 514/899; 536/102

[56] References Cited

U.S. PATENT DOCUMENTS

| | | |
|---|---|---|
| 59,756 | 1/1866 | Benedict . |
| 1,580,400 | 4/1926 | Bommarito . |
| 2,022,729 | 12/1935 | Malisoff . |
| 2,385,394 | 4/1945 | Witte . |
| 2,816,854 | 12/1957 | Gross . |

(List continued on next page.)

FOREIGN PATENT DOCUMENTS

| | | |
|---|---|---|
| 572682 | 3/1959 | Canada . |
| 876101 | 7/1971 | Canada . |
| 910816 | 9/1972 | Canada . |
| 1171410 | 7/1984 | Canada . |
| 1287583 | 8/1991 | Canada . |
| 1336889 | 9/1995 | Canada . |
| 0006340 | 1/1980 | European Pat. Off. . |
| 0035882 | 9/1981 | European Pat. Off. . |
| 0124774 | 11/1984 | European Pat. Off. . |
| 0377266 | 7/1990 | European Pat. Off. . |
| 2318649 | 7/1975 | France . |
| 197385 | 5/1967 | Russian Federation . |
| 124440 | 2/1928 | Switzerland . |
| 406964 | 3/1934 | United Kingdom . |
| 668968 | 3/1952 | United Kingdom . |
| 2079149 | 1/1982 | United Kingdom . |
| 85/02422 | 6/1985 | WIPO . |
| 90/07339 | 7/1990 | WIPO . |
| 92/17190 | 10/1992 | WIPO . |

OTHER PUBLICATIONS

Bloomer et al., "Estrogen receptor–mediated cytotoxicity using iodine–125" *J. Cell. Biochem.* (1983) 21:39–45.

Bloomer et al., "Estrogen receptor–mediated cytotoxicity using iodine–125" *Chem. Abstracts* (1983) 99:(Abstract No. 136212x).

Bloomer et al., "Iodine–125–labelled tamoxifen is differently cytotoxic to cells containing oestrogen receptors" *Int. J. Radiat. Biol.* (1980) 38(2):197–202.

Bloomer et al., "Iodine–125–labelled tamoxifen is differently cytotoxic to cells containing oestrogen receptors" *Chem. Abstracts* (1981) 94:(Abstract No. 94:41160m).

(List continued on next page.)

*Primary Examiner*—Raj Bawa
*Attorney, Agent, or Firm*—Morrison & Foerster LLP

[57] ABSTRACT

The present invention is concerned with the use of starch containing amylose as a complexant with iodine for preparing dry powder pharmaceutical formulations useful in the preparation of capsules or tablets. The helical structure of the amylose molecule and its ability to complex. with smaller molecules including iodine make starch (amylose) a desirable vehicle for the administration of iodine ($I_2$) as a dry powder formulation in capsule or tablet form. These pharmaceutical formulations are particularly useful in the treatment of or the prevention of iodine deficiency diseases including breast dysplasia, breast cancer, endometriosis, premenstrual syndrome and radiation sickness from nuclear fallout.

9 Claims, 1 Drawing Sheet

U.S. PATENT DOCUMENTS

| | | |
|---|---|---|
| 2,927,058 | 3/1960 | Minto . |
| 3,881,991 | 5/1975 | Kurimoto et al. . |
| 3,888,739 | 6/1975 | Whetzel et al. . |
| 4,010,259 | 3/1977 | Johansson . |
| 4,012,504 | 3/1977 | Eckols . |
| 4,230,503 | 10/1980 | Hughes . |
| 4,279,940 | 7/1981 | Wurzburg et al. . |
| 4,384,960 | 5/1983 | Polley . |
| 4,564,521 | 1/1986 | Altadonna . |
| 4,729,948 | 3/1988 | Saruhashi et al. . |
| 4,737,459 | 4/1988 | Zeikus et al. . |
| 4,744,975 | 5/1988 | Suami et al. . |
| 4,755,397 | 7/1988 | Eden et al. . |
| 4,816,255 | 3/1989 | Ghent et al. . |
| 4,867,967 | 9/1989 | Crutcher . |
| 4,886,661 | 12/1989 | Guy et al. . |
| 5,171,582 | 12/1992 | Ghent et al. . |
| 5,250,304 | 10/1993 | Ghent et al. . |
| 5,389,385 | 2/1995 | Ghent et al. . |
| 5,589,198 | 12/1996 | Eskin et al. . |

OTHER PUBLICATIONS

Bluhm et al., "Detailed structure of the $V_h$–amylose–iodine complex: a linear polyiodine chain" *Carbohydrate Research* (1981) 89:1–9.

Dyer, "An Index of Tumor Chemotherapy" *N.I.H.* (1949) pp. 10–12, 22, 23.

Eskin et al., "Replacement therapy with iodine in breast neoplasia" *Intl. J. Gynecol. Obstet.* (1970) 8(2):232(Abstract No. 354).

Eskin et al., "Etiology of mammary gland pathophysiology induced by iodine deficiency" *Frontiers in Thyroidology* (1986) G. Medeiros–Neto and E. Gaitan (eds.), Plenum Medical Book Company, New York 2:1027–1031.

Eskin et al., "Human breast uptake of radioactive iodine" *Obstetrics and Gynecology* (1974) 44(3):398–402.

Eskin., "Iodine and breast cancer—a 1982 update" *Biological Trace Element Research* (1983) 5:399–412.

Eskin, "Iodine metabolism and breast cancer" *Trans. N.Y. Acad. Sci.* (1970) 32(8):911–947.

Eskin, "Iodine metabolism and breast cancer" *Chem. Abstracts* (1971) 75:237(Abstract No. 17655p).

Eskin., "Thyroid hormones and tumor development" *Influences of Hormones in Tumor Development* (1979) Franklin Publishers, (Chapter 6) pp. 130–156.

Eskin, B.A., "Iodine and mammary cancer" *Adv. Exp. Med. Biol.* (1978) 91:293–304.

Eskin, B.A., "Iodine and mammary cancer" *Chem. Abstracts* (1979) 90:337 (Abstracts No. 135752a).

Ghent et al., "Fibrocystic breast dysplasia: A deficiency syndrome" *Clin. Invest. Med.* (Canada) (1986) 9(3):A66(Abstract No. R–406).

Ghent, "Elemental iodine supplementation in clinical breast dysplasia" *Proc. 77th Annual Meeting Amer. Assoc. Cancer Res.* (1986) 27:189(Abstract No. 751).

Handa et al., "On the blue color of triiodide ions in starch and starch fractions. II. Characterization of the changes in absorption and circular dichroism spectra triiodide icons in amylose with the DP" *Biopolymers* (1980) 19:723–740.

*Harrison's Principles of Internal Medicine,* (1984) Isselbacher et al., (eds.) 13th edition, Part 5: Nutrition, Table 71–4.

Hatch, "Effect of temperature on the starch–iodine spectrophometric calibration line" *Anal. Chem.* (1982) 54(12):2002–2005.

Hetzel, "Iodine deficiency disorders (IDD) and their eradication" *Lancet* (1983) 12: 1126–1129.

Honour et al., "Secretion of radioiodine in digestive juices and milk in man" *Clin. Science* (1952) 11:447–462.

Kelly et al., "Prevalence and geographical distribution of endemic goitre" *W.H.O. Monograph,* 44: 27–35.

Kemp et al., *Organic Chemistry* (1980) Worth Publishers, Inc., Chapter 27, pp. 992–994.

Larson et al., "Amperometric method for determining the sorption of iodine by starch" *anal. Chem.* (1953) 25:802–804.

*Martindale, The Extra Pharmacopoeia,* 29th Edition, (1989) Reynolds (ed.), The Pharmaceutical Press, London, p. 1185.

Moossa et al., "Thyroid status and breast cancer"*Ann. Roy. Coll. Surg. Engl.* (1973) 53:178–188.

Pennington, "A review of iodine toxicity reports" *Journal of the American Dietetic Association* (1990) 90:1571–1581.

Robyt, "In vivo conversion of starch to D–glucose" *Starch Chemistry and Technology,* pp. 106–108.

Derwent Patent Database Abstract of Russian Patent No. 197385 to Mokhnach (May 31, 1967), 1 page total.

Song et al., "Resistance of the *Giarda lamblia* cysts to various disinfectants" *Chem. Abst.* (1984) 101:389–390(Abstract No. 126735r).

Stringer et al., "Comparison of bromine, chlorine & iodine as disinfectants for amoebic cysts" *Disinfection—Water & Wastewater* (1975), pp. 193–209.

Stringer et al., "Comparison of bromine, chlorine & iodine as disinfectants for amoebic cysts" Chem. Abstracts (1976) 84:299 (Abstract No. 126316k).

Strum et al., "Resting human female breast tissue produces iodinate protein" *J. Ultrastructure Res.* (1983)84:130–139.

Takeda et al., "Structures and amounts of branched molecules in rice amyloses" *Carbohydrate Research* (1989) 186:163–166.

Takeda et al., "Structures of indica rice starches (IR48 and IR64) having intermediate affinities for iodine" *Carbohydrate Research* (1989) 187:287–294.

Takeda et al., "Structures of rice amylopectins with low and high affinities for iodine" *Carbohydrate Research* (1987) 168:79–88.

*U.S. Pharmacopea XVIII* (1970) pp. 733–734.

Vishnyakova et al., "On the treatment of dyshormonal hyperplasia of mammary glands" *Vestin. Akad. Med. Mawk. U.S.S.R.* (1966) 21:26–31.

Yunbing et al., "Clinical observation of 174 cases of hyperplastic cystic disease of breast treated with traditional Chinese medicine" *J. Traditional Chinese Medicine* (1983) 3(4):291–294.

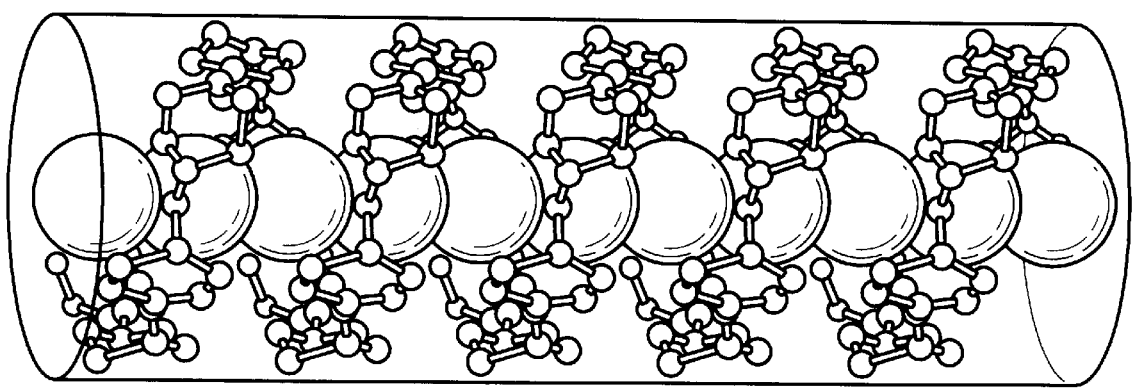

DRY STARCH-IODINE PHARMACEUTICAL FORMULATIONS

REFERENCE TO RELATED APPLICATIONS

This application is a continuation in part of Ser. No. 08/593,467, filed Jan. 29, 1996, which is a continuation in part of Ser. No. 08/272,308, filed Jul. 8, 1994, now abandoned, which is a continuation of Ser. No. 07/961,038, filed Oct. 14, 1992, now abandoned, which is a continuation of Ser. No. 07/676,170, filed Mar. 28, 1991, now abandoned.

BACKGROUND OF THE INVENTION

The present invention is concerned with the use of starch containing amylose as a complexant with iodine for preparing dry powder pharmaceutical formulations useful in the preparation of capsules or tablets.

More particularly, the invention is concerned with the administration of molecular iodine ($I_2$) to patients suffering from iodine deficiency diseases. Heretofore, $I_2$ has been administered to patients in aqueous molecular form. The administration of aqueous molecular iodine to patients has several disadvantages including the need for specialized dispensers utilizing selective membranes thereby preventing the patient from ingesting crystallized iodine. Standardization of daily dosage is also a problem associated with these dispensers. See U.S. Pat. No. 4,384,960 to Polley.

In view of the apparent disadvantages to the administration of aqueous molecular iodine, it became evident that it would be desirable to administer the iodine in capsule or tablet form. The present invention is directed to dry pharmaceutical formulations containing iodine and the administration of the same in capsule or tablet form. This mode of administration of iodine is believed to be superior to those prior art methods and overcomes the various disadvantages experienced by the administration of elemental iodine in aqueous form.

In general, starch contains about 20 percent of a water-soluble fraction called amylose, and 80 percent of a water-insoluble fraction called amylopectin. These two fractions appear to correspond to different carbohydrates of high molecular weight and formula $(C_6H_{10}O_5)_n$. Upon treatment of acid or under the influence of enzymes, the components of starch are hydrolized progressively to dextrin which is a mixture of low-molecular-weight polysaccharides, (+)-maltose, and finally D-(+)-glucose. Both amylose and amylopectin are made up of D-(+)-glucose units, but differ in molecular size and shape.

Of particular interest is the structure of amylose which is a linear 1,4-acetal polymer of glucose. Thus, amylose is made up of chains of many D-(+)-glucose units, each in and joined by an α-glycoside linkage to C-4 of the next glucose unit. It is the alpha linkage at the acetal carbon which has a profound effect on the overall shape of the giant amylose molecule which gives it its unique physical properties and the interactions the amylose molecule may have with smaller molecules.

Amylose is a helical molecule, with glucose residues that coil back on each other, creating a loosely overlapping spiral with a central cavity or tube.

A variety of small molecules including iodine, form weak complexes with amylose. As is known, the starch-iodine complex has a deep blue-violet colour that can be used to test for the presence of either amylose or iodine. From structural evidence, it is apparent that the colour arises because of interactions between rows of $I_3^-$ molecules oriented end to end inside the tubular cavity of amylose structure (see *Organic Chemistry*, Kemp-Vellaccio, Worth Publishers, Inc., copyright 1980, p. 994).

It is the unique physical properties of the amylose molecule which forms a part of starch which has led us to believe that starch would be ideally suited as a complexant for iodine to prepare dry pharmaceutical formulations which may be encapsulated in capsule or pill form for oral administration. These dry formulations of iodine would be superior to known aqueous iodine solution used in the treatment of iodine deficiency diseases such as breast dysplasia, breast cancer, endometriosis and premenstrual syndrome. Such aqueous formulations are contemplated in U.S. Pat. No. 4,816,225 to Ghent et al issued Mar. 28, 1989, and WO90/07339, published Jul. 12, 1990. Dry powder formulations of the present form in capsule or tablet form are also useful in the treatment of radiation sickness from nuclear fallout and the like and are more easily administrable in oral form to patients. See for example U.S. Pat. No. 4,384,960 to Polley which discloses a dispenser of aqueous elemental iodine for oral administration to prevent or cure iodine-deficient goiter.

SUMMARY STATEMENT OF THE INVENTION

The present invention therefore relates to the preparation of a dry form of elemental iodine ($I_2$) which may be encapsulated in capsule or pill form for therapeutic oral administration to patients.

More particularly, the invention relates to the use of starch and more particularly to the use of amylose contained in starch as a complexant with iodine (aqueous molecular iodine, i.e. $I_2$) to provide means to prepare a dry powder formulation in capsule or tablet form for oral administration to patients suffering from or for prevention of various iodine deficiency diseases and the like.

BRIEF DESCRIPTION OF THE DRAWING

FIG. 1 is a molecular representation of the amylose-iodine complex wherein the iodine molecules depicted as solid spheres fit within the cavity of the amylose helices.

DESCRIPTION OF THE PREFERRED EMBODIMENTS

The present invention is concerned with utilizing starch as a complexant with iodine to form an iodine-starch complex and more specifically with the use of the amylose component of starch to form an amylose-iodine complex as depicted in FIG. 1. (Taken from Organic *Chemistry*, Kemp-Vellaccio, Worth Publishers, Inc. 1980, p. 994.)

It is mostly the linear component of the amylose in starch which is responsible for the uptake of iodine. This starch-iodine complex exists in a helical configuration as depicted in FIG. 1 within which the triiodide ions ($I_3^-$) or polyiodide ions ($I_5^-$) up to $I_{11}^-$ reside. The most common complex however is the triiodide ion-amylose complex. The molecular weight or molecular weight distribution of the starch (amylose) plays a critical factor in the ability of starch to complex iodine.

The minimum length of the amylose chain to produce its characteristic blue colour is about 30–40 D-glucose units, providing a cavity corresponding closely in length to an 11-atom polyiodine chain. Therefore, the brand, lot, quality, source, time of harvesting and place of growth are all factors which will influence the linear amylose content of the starches. A preferred starch for use in the preparation of the starch-iodine formulation is #7 Hylon starch. This starch is a purified "specialty" starch produce by Nacan Products of Toronto, Ontario, Canada. The starch is made from a hybrid corn called Hylon #7 which contains 70 percent amylose and 30 percent amylopectin. From the use of such a specialty starch containing a high proportion of amylose, the amount of iodine in the complex is now determined from the amount of iodine supplied to the complex rather that the amount of iodine that can be bound by the starch amylose.

In the preparation of the iodine-starch (amylose) complex, since the iodine will ultimately be used to treat human patients, high quality re-sublimed iodine should be employed in the preparation.

In determining a method for the production of the desired iodine-starch complex, the effect of temperature on the capacity of starch to absorb iodine must be examined. The effective temperature is best described by Hatch (*Analytical Chemistry*, vol. 54, 2002 (1982). At higher temperature (especially at 60° C.), there is a temperature-dependant change in the structure and (or) number of starch helices available for reaction with iodine (triiodide ions). In fact, the thermal decoloration of the blue starch-iodine complex is the result of thermally induced deterioration or unravelling of the starch helices from around the iodine (triiodide ions ($I_3^-$) or others)). This phenomenon is called hysteresis effect and is reversible at least up to 40° C. As discussed by Hatch supra, the complex does not decolorize completely until warmed to 38° C. (±1° C.) which is essentially at body temperature.

As noted above, the complexing of the iodine with starch is primarily in the form of triiodide ions ($I_3^-$). The present invention, however, is primarily concerned with the preparation of a dry formulation of iodine for oral consumption to supply elemental iodine ($I_2$) for treatment of iodine deficiency diseases and the like.

In order to understand how $I_2$ is supplied to the patient, one must understand how iodine in predominately triiodide form is released from starch. There are three different methods for releasing the iodine from the starch molecule which include:

a) thermally which induces the unfolding of the amylose helices;

b) by acid hydrolysis of starch down to D-glucose in aqueous solutions; or c) by α-amylase treatment.

For a detailed description of the last two methods see, for example, Robyt, *Starch, Chemistry and Technology*, p. 94.

It is the latter treatment, i.e. that of α-amylase which is involved in the in vivo degradation of starch. Salivary α-amylase degrades starch (amylose) to maltose (a disaccharide) and to higher oligosaccharides. In the stomach, the further α-amylase activity causes further starch degradation and liberation of iodine ($I_3^-$). The other enzymes which further degrade these fragments are glucosidases (α-1→4 and α-1→6). These enzymes are secreted by the brush border cells of the lining of the small intestine and by the pancreas. These enzymes do not have any action on starch per se, but their combined action completes the job of converting starch into D-glucose.

Thus, it can be seen from the foregoing, that once the encapsulated starch-iodine complex is ingested, it is acted upon by the upper small bowel contents including α-amylase, bile and pancreatic enzymes containing amylase and glucosidases. The amylase, aided by bile, will digest the amylose and thereby release the $I_3^-$ from the complex.

$I_3^-$ cannot exist as a molecule (uncomplexed) and immediately changes to $I_2$ and I. The I is picked up by the sodium, potassium and proteins of the food stuffs to produce iodides, while the $I_2$ is absorbed as $I_2$ in the same fashion as $I_2$ administered in an aqueous vehicle.

It can be seen from the foregoing, that the starch-iodine ($I_3^-$) complex is ideally suited to produce a dry formulation for oral administration of iodine due to the immediate conversion of the triiodide ion to $I_2$ in vivo.

The starch-iodine complex of the present invention can generally be prepared by the following method. In this preferred method, the preferred starch, #7 Hylon is used. This specialized starch is exposed to aqueous molecular iodine (AMI) at room temperature (20° C.) (300 milligrams iodine per liter) in a ratio of 1 gram of starch to 100 milliliters AMI for 12 hours at 20° C.

The iodine solution is prepared by exposing 50 grams of prilled iodine to ion-free water at 20° C. for 4 days.

The chemical reaction of this combination is

$$I_2+H_2O=HOI+I+I_2+I_3.$$

The proportion of $I_2$ and $I_3$ are temperature dependant as noted above, with an increased temperature increasing the amount of $I_3$.

The solution is passed through a micropore filter and is then ready for combination with the starch. The AMI solution combines with the amylose of starch and produces a complex of $I_3$ with the amylose helices. The $I_2$ and I present in the AMI solution are compressed in the helices to $I_3$. It is this combination that produces the calorimetric change to blue.

After exposure of the AMI to starch for 12 hours, the supernatant water is decanted and tested for presence of iodine.

The resulting starch-iodine complex is allowed to dry at room temperature and then mechanically pulverized. It is now ready for encapsulation, preferably at a strength of 3 milligrams of iodine in 100 milligrams of the complex.

The above dosage of 3 milligrams of iodine in 100 milligrams of the complex is the preferred daily dosage for the treatment of iodine deficiency diseases such as breast dysplasia, breast cancer, endometriosis and premenstrual syndrome as disclosed WO90/07339 to Ghent et al, published Jul. 12, 1990.

The ideal complex would contain 3 milligrams of $I_2$ in 100 milligrams starch so that direct encapsulation without fillers could be used. However, the amount of iodine/amylose configuration could be changed if encapsulation required it.

It is to be understood that the recommended daily dosage of $I_2$ for the treatment of other iodine related diseases such as with the thyroid including radiation sickness etc. may be other than the preferred dosage disclosed hereinabove and thus variation of the amount of aqueous molecular iodine supplied to starch may be increased or decreased depending on the dosage required. Specialty starches such as #7 Hylon starch with its high amylose content are uniquely suited for complexing of an increased amount of iodine and as indicated previously the amount of iodine in the complex is a function of the amount of iodine supplied to the complex rather than the amount of iodine. that can be bound by the starch amylose. Other less amylose rich starches may be used however provided there is sufficient amylose present to supply the desired dosage of iodine.

Although the use of additional pharmaceutical adjuvants is believed not to be required, suitable pharmaceutical adjuvants, fillers, excipients etc. may form part of the pharmaceutical composition if desired.

Since the present invention is subject to many modifications, variations and changes in detail, it is intended that all matters in the foregoing description or shown in the accompanying drawing be interpreted as illustrative and not in a limiting sense.

The embodiments of the invention in which an exclusive property or privilege is claimed are defined as follows:

1. A dry starch-iodine complex suitable for oral administration of iodine in capsule or pill form, wherein said starch-iodine complex is a non-covalent complex of starch and iodine.

2. The starch-complex of claim 1 wherein the starch contains 70% amylose and 30% amylopectin.

3. A dry pharmaceutical composition useful in the treatment of iodine deficiency diseases including breast dysplasia, breast cancer, endometriosis and premenstrual syndrome as well as other iodine related diseases, said composition comprising the dry starch-iodine complex of claim 1.

4. The pharmaceutical composition of claim 1 wherein the starch-iodine complex 3 milligrams of $I_2$ per 100 milligrams of starch.

5. The pharmaceutical composition of claim 3 wherein the starch-iodine complex contains 70% amylose and 30% amylopectin.

6. A process for preparing a starch-iodine complex as defined in claim 1 characterized by exposing starch having a suitable amylose component to aqueous molecular iodine (AMI) at room temperature (20° C.) for sufficient period of time to allow complexing to occur.

7. The process of claim 6, further comprising drying the starch-iodine complex at room temperature (20° C.) followed by mechanical pulverization thereof thereby producing a dry powder starch-iodine complex.

8. A pharmaceutical tablet comprised of a dry starch-iodine complex formulation, wherein said starch-iodine complex is a non-covalent complex of starch and iodine. added.

9. The pharmaceutical composition of claim 4 wherein the starch of the starch-iodine complex contains 70% amylose and 30% amylopectin.

* * * * *